United States Patent
Rombach

(10) Patent No.: US 11,141,217 B2
(45) Date of Patent: Oct. 12, 2021

(54) PROBE APPLICATOR

(71) Applicant: Erbe Elektromedizin GmbH, Tuebingen (DE)

(72) Inventor: Thorsten Rombach, Gomaringen (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 268 days.

(21) Appl. No.: 16/216,301

(22) Filed: Dec. 11, 2018

(65) Prior Publication Data

US 2019/0175261 A1 Jun. 13, 2019

(30) Foreign Application Priority Data

Dec. 12, 2017 (EP) .................................... 17206694

(51) Int. Cl.
*A61B 18/14* (2006.01)
*A61B 1/005* (2006.01)
(Continued)

(52) U.S. Cl.
CPC ........ *A61B 18/1482* (2013.01); *A61B 1/0052* (2013.01); *A61B 17/3417* (2013.01);
(Continued)

(58) Field of Classification Search
CPC ....... A61B 1/0052; A61B 1/0051; A61B 1/01; A61B 1/3132; A61B 10/04; A61B 17/3421; A61B 17/3417; A61B 18/1402; A61B 18/1482; A61B 2017/003; A61B 2017/00477; A61B 2018/001; A61B 2018/00184; A61B 2018/00011; A61B 2018/00017; A61B 2018/00178;
(Continued)

(56) References Cited

U.S. PATENT DOCUMENTS 5,314,406 A * 5/1994 Arias .................. A61M 3/0233
604/21
6,761,698 B2 * 7/2004 Shibata .......... A61B 17/320068
601/2
(Continued)

FOREIGN PATENT DOCUMENTS

CN 204147118 U * 2/2015 ............. A61B 18/14
CN 204147118 U 2/2015
(Continued)

OTHER PUBLICATIONS

Extended European Search Report dated Feb. 21, 2018, for EP Application No. 17206694.6 (7 pgs.).
(Continued)

*Primary Examiner* — Sean P Dougherty
*Assistant Examiner* — Alexander H Connor
(74) *Attorney, Agent, or Firm* — Fitch, Even, Tabin & Flannery LLP

(57) ABSTRACT

According to the invention, there is provided a probe applicator (10) disposed for receiving flexible probes (11) that are intended for endoscopic use and can be made accessible with the probe applicator for laparoscopic use. The control of the device supplying the probes (11) occurs via control elements (32, 33) of the probe applicator (10). Preferably, the probe (11) is supplied via a connecting device (38) provided on the probe applicator (10).

14 Claims, 4 Drawing Sheets

(51) Int. Cl.
*H01R 13/00* (2006.01)
*A61B 17/34* (2006.01)
*A61B 18/00* (2006.01)
*A61B 17/00* (2006.01)

(52) U.S. Cl.
CPC ....... *A61B 17/3421* (2013.01); *H01R 13/005* (2013.01); *A61B 2017/003* (2013.01); *A61B 2017/00477* (2013.01); *A61B 2018/00178* (2013.01); *A61B 2018/00184* (2013.01); *A61B 2218/002* (2013.01); *H01R 2201/12* (2013.01)

(58) Field of Classification Search
CPC .. A61B 2218/002; A61M 2025/09175; A61M 25/0068; A61M 25/09; H01R 13/005; H01R 2201/12
See application file for complete search history.

(56) References Cited

U.S. PATENT DOCUMENTS

| | | | |
|---|---|---|---|
| 2012/0253116 A1* | 10/2012 | Sniffin | A61B 1/00105 600/106 |
| 2013/0331825 A1* | 12/2013 | Mitchell | A61B 18/1492 606/1 |
| 2014/0236147 A1 | 8/2014 | Schneider | |
| 2016/0015374 A1* | 1/2016 | Gifford | A61B 17/3439 600/201 |
| 2017/0319233 A1* | 11/2017 | Fonger | A61B 17/3421 |
| 2018/0014869 A1* | 1/2018 | Gogolin | A61B 18/1482 |

FOREIGN PATENT DOCUMENTS

DE 10354147 A1 6/2005
RU 2460551 C1 9/2012

OTHER PUBLICATIONS

Russian Office Action dated May 31, 2021, in corresponding Russian Application No. 2018142844/14, with machine English translation (12 pages).

* cited by examiner

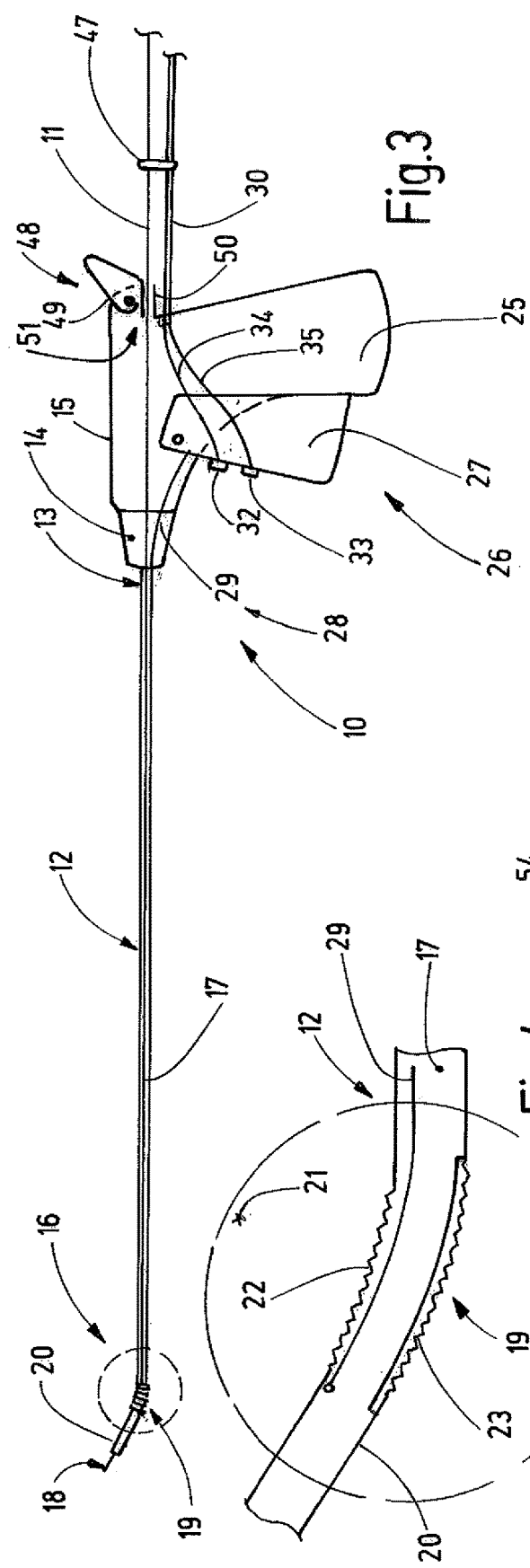
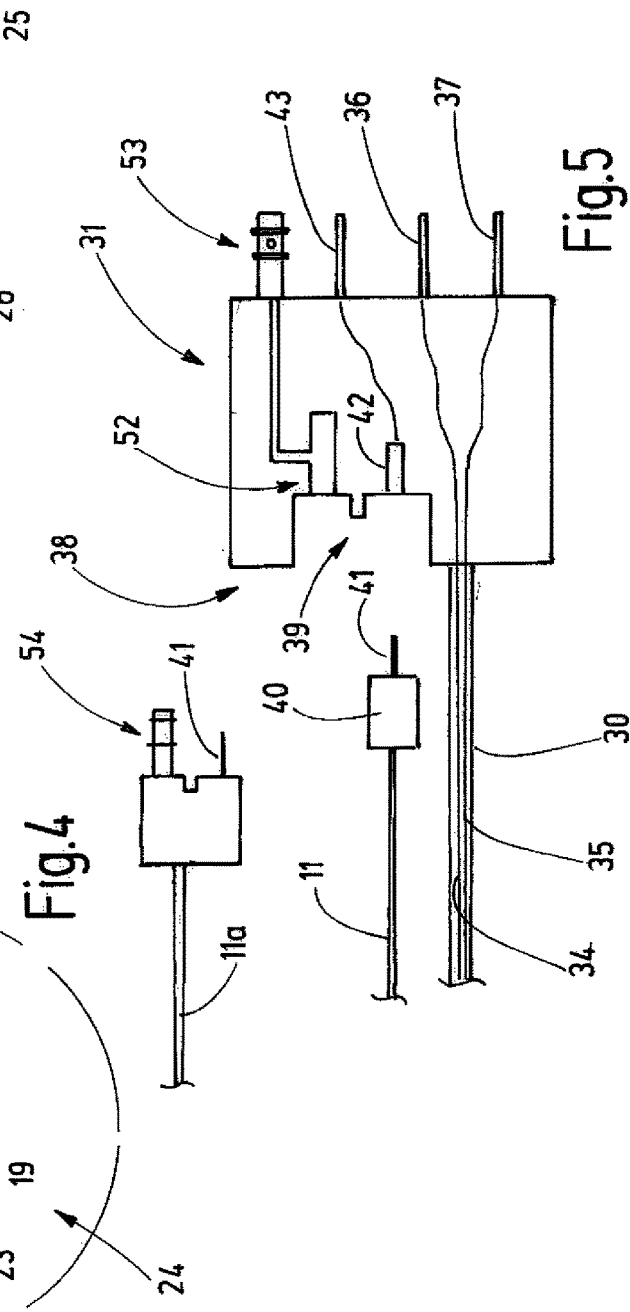

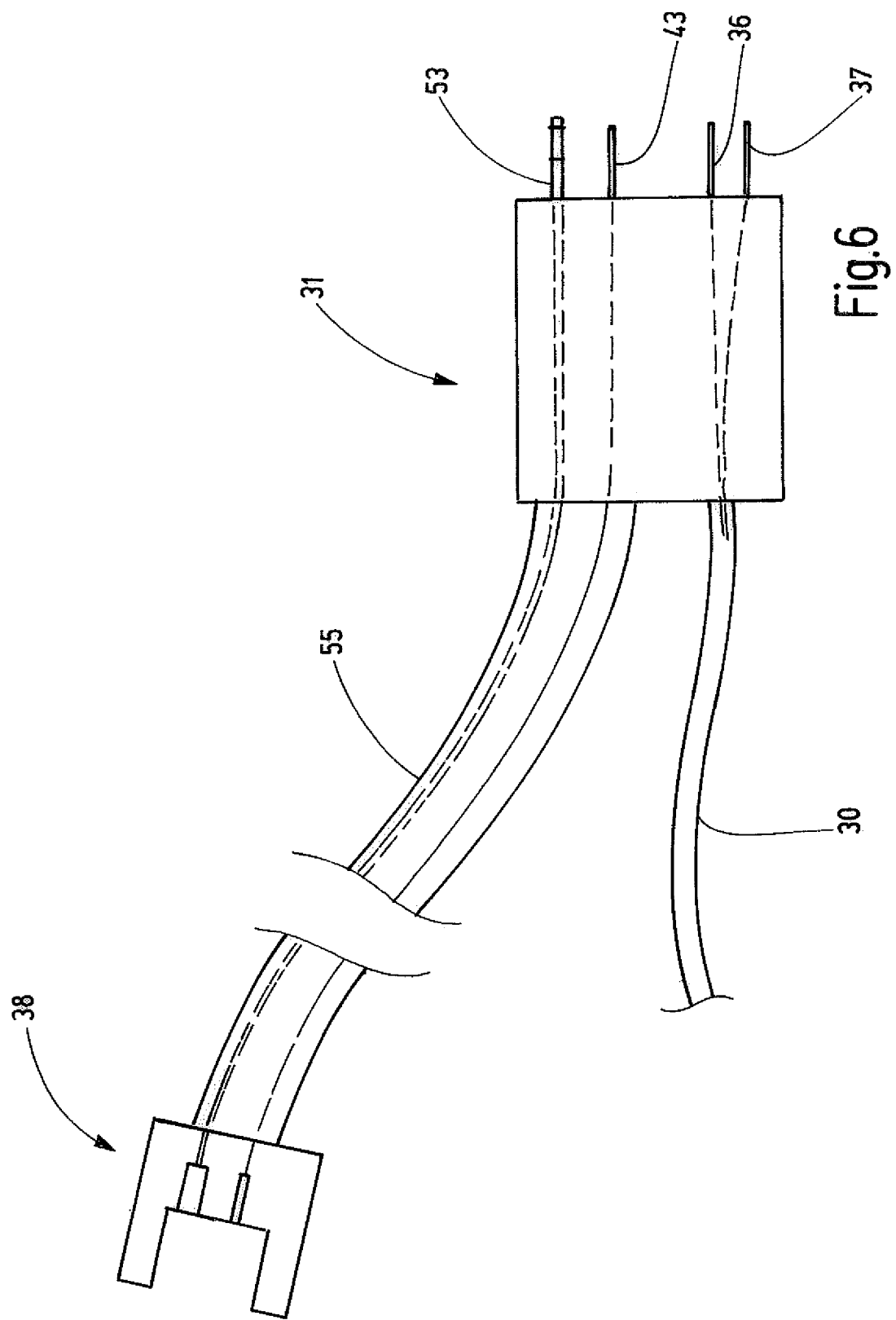

PROBE APPLICATOR

RELATED APPLICATION(S)

This application claims the benefit of European Patent Application No. 17206694.6, filed Dec. 12, 2017, the contents of which are incorporated herein by reference as if fully rewritten herein.

TECHNICAL FIELD

The subject matter of the invention is an applicator for the laparoscopic use of flexible probes.

BACKGROUND

Publication U.S. Pat. No. 5,314,406 discloses a medical instrument having an elongated shaft whose proximal end is held on a housing having a handle. On the side of the housing opposite the shaft, there is provided an insertion opening through which the probe can be inserted through the housing into the shaft. The probe extends through the shaft and may project therefrom on the distal end of said shaft. The shaft is disposed for aspirating fluids from the treatment site, which can be controlled via appropriate valves on the handle. The handle of the housing has connections for the fluid line for rinsing and aspirating. In turn, the probe is connected to an electrical power source.

Considering this, it is the object of the invention to provide a probe applicator that allows the use of flexible probes outside endoscopic applications.

SUMMARY

This object is achieved with the probe applicator as described herein.

The probe applicator according to the invention comprises a housing with a shaft that is an elongated stiff tube whose proximal end is connected to the housing. The shaft is open on both its ends. The shaft is substantially stiffer than the probes to be slid through it. The stiffness of the shaft is preferably great enough that a transverse force of 0.5 N acting on the distal end of the shaft having a length of, e.g., 200 mm to 400 mm, effects a lateral, elastic deflection of the shaft, said deflection not being greater than 75 mm. If necessary, the shaft may be stiffer, so that, e.g., considering said length and said force, only a deflection of 6 mm or less occurs.

On the side of the housing opposite the shaft, there is provided a probe insertion opening through which a flexible probe can be slid into the housing and through said housing into the shaft. The housing into which the probe has been inserted can then be manually positioned and moved by means of the handle provided on the housing in order to insert the shaft—for example, through a small access opening—into the body of the patient in order to perform the desired surgical procedures by activating the probe and moving the housing with the shaft. To do so, one or more control elements for activating and deactivating the probe are arranged on the housing, in particular on the handle of said housing.

Extending from the housing, there is a cable to a plug in order to transmit a signal originating from an actuation of the control element to a plug or another connector. The signal conductor extending through the cable may be an electrical line, a fluid line, a waveguide such as, for example, an optical fiber or the like.

In addition, the probe applicator comprises a connecting device that is disposed for connecting a probe in order to supply said probe with operating medium. The operating medium may be electrical power, a liquid or gaseous fluid, photoenergy or the like. Preferably, the connecting device is provided on the plug, via which the probe applicator is to be connected to a supply device. Alternatively, it is also possible to configure the connecting device separate from the plug and, for example, provide it in the form of a jack arrangement that is connected to the plug via a flexible line. The connecting device may also be provided on the housing.

The probe applicator according to the invention allows the use of a plurality of flexible probes known in endoscopy outside of endoscopes. For example, the user can employ the probe applicator as in laparoscopic procedures. In doing so, endoscopic probes will become usable in surgical disciplines such as in general surgery, visceral surgery, gynecology, urology and in the field of ear nose and throat (ENT) surgery.

The rigid shaft of the probe applicator stabilizes the flexible probes over and up to a length of 45 centimeters or more. Thus, flexible probes can be used in laparoscopy and mini-laparoscopy, without requiring separate rigid instruments performing the same function.

Furthermore, the probe applicator according to the invention makes possible the use of the probes, in particular in the manner of a manual actuation, which is an important aspect in surgical applications. The surgeon is able to position, move and guide, as well as activate and deactivate, the probe with one hand on the housing, i.e., on the handle and by means of the control elements provided thereon.

The shaft is slim and long, while its diameter is preferably at most 5 mm and, in some applications, at most 3 mm. The length of the shaft preferably exceeds at least 100 mm, furthermore, preferably at least 350 mm or 450 mm. The shaft is stiff, in particular rigid in compression and flexurally rigid, in order to be able to position and move its distal end in the body of the patient by moving the handle and the housing in a targeted manner.

In a preferred embodiment a bending device is arranged on the distal end of the shaft, said device, for example being configured as a flexible, tube-shaped section, a bellows-like section or the like, that can be converted from an extended straight form into an arcuate form. In doing so, it is sufficient if the bending device is able to perform a pivoting movement about a single axis. In doing so, the flexible section bends about an axis of curvature, said axis extending transversely with respect to the shaft and not intersecting said shaft. Preferably, the bending device exhibits only one degree of freedom of movement, namely one degree of freedom of a pivoting motion. The shaft may have an additional degree of freedom, namely a rotation about its longitudinal axis.

For the orientation of an angled end of the shaft in various spatial directions, the shaft may be rotated by moving the housing or, alternatively, by rotating the shaft on the housing about its longitudinal direction. In doing so, the surgeon can move the end of the probe projecting from the shaft toward the envelope of cone, in which case the opening angle of this cone can be varied by adjusting the bending device.

Furthermore, the probe insertion opening may be provided with a locking device for the axial fixation of the probe, so that the surgeon can distally move the probe out of the shaft or retract said probe into said shaft, and then fix said probe in position.

BRIEF DESCRIPTION OF THE DRAWINGS

Additional details of advantageous embodiments of the invention are the subject matter of the drawings, the descrip- The drawings illustrate examples of embodiment of the invention. They show in FIG. 1, a simplified perspective representation of a probe applicator with a probe, FIG. 2, a simplified perspective representation of the probe applicator according to FIG. 1 without a probe, FIG. 3, a schematic side elevation of the probe applicator with a probe, FIG. 4, an enlarged schematized representation of a bending device provided on the shaft of the instrument, FIG. 5, the plug of the probe applicator with two different probes that can be inserted in the plug, and FIG. 6, a schematized side elevation of a modified embodiment of a plug and the connecting device provided for the probes.

DETAILED DESCRIPTION

Figure 1:
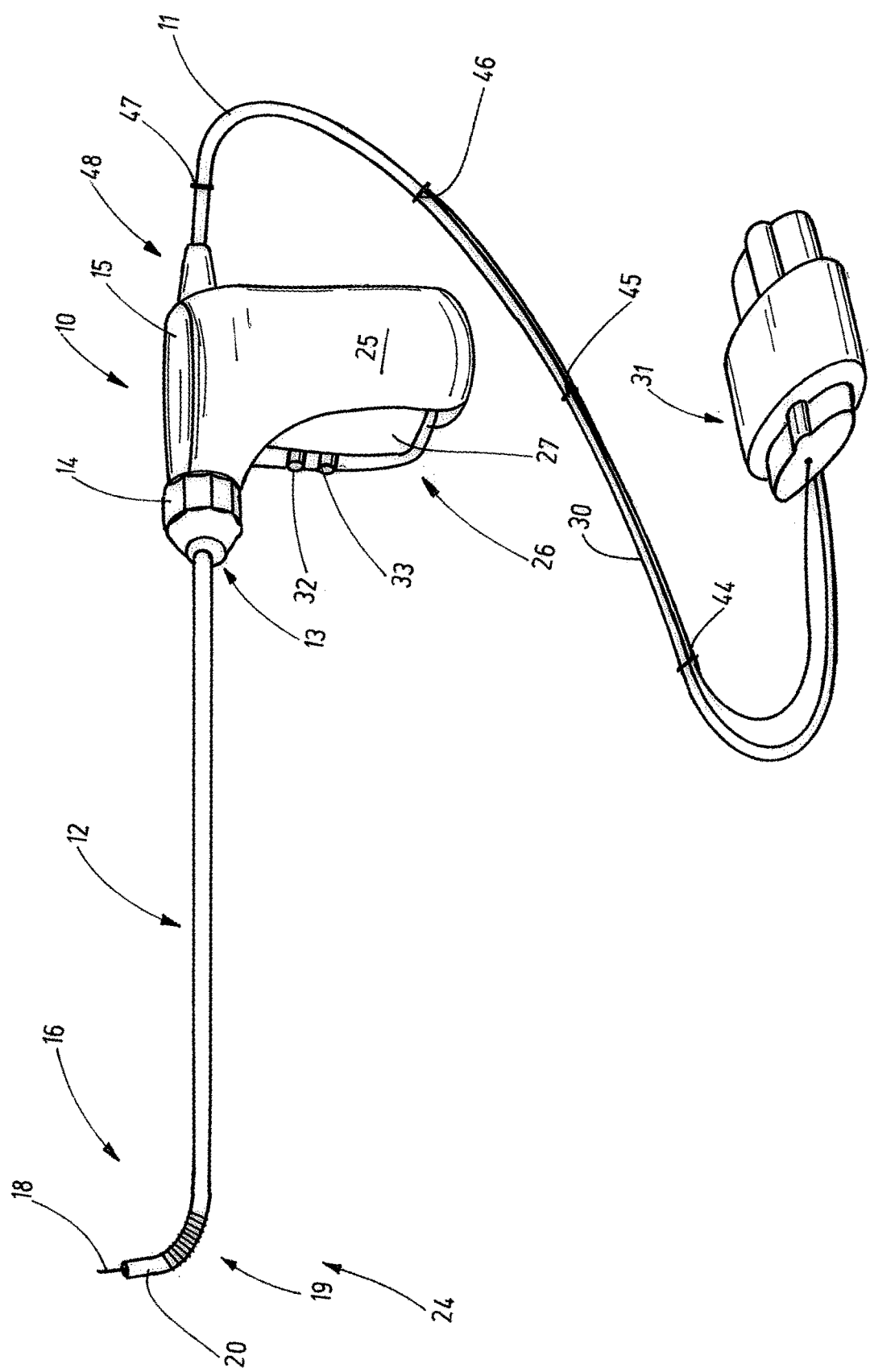

FIG. 1 shows a probe applicator 10 that is disposed for receiving flexible probes such as, for example, the probe 11, so as to be able to perform laparoscopic procedures with this probe 11. To accomplish this, the probe applicator 10 comprises, in the manner of a laparoscopic instrument, an elongated shaft 12 whose proximal end 13 is held in or on a shaft receptacle 14. Preferably, the shaft receptacle 14 can be rotated about the longitudinal axis of the shaft 12; however, it may also be rigid, i.e., be non-rotatably configured or arranged relative to a housing 15.

Figure 2:
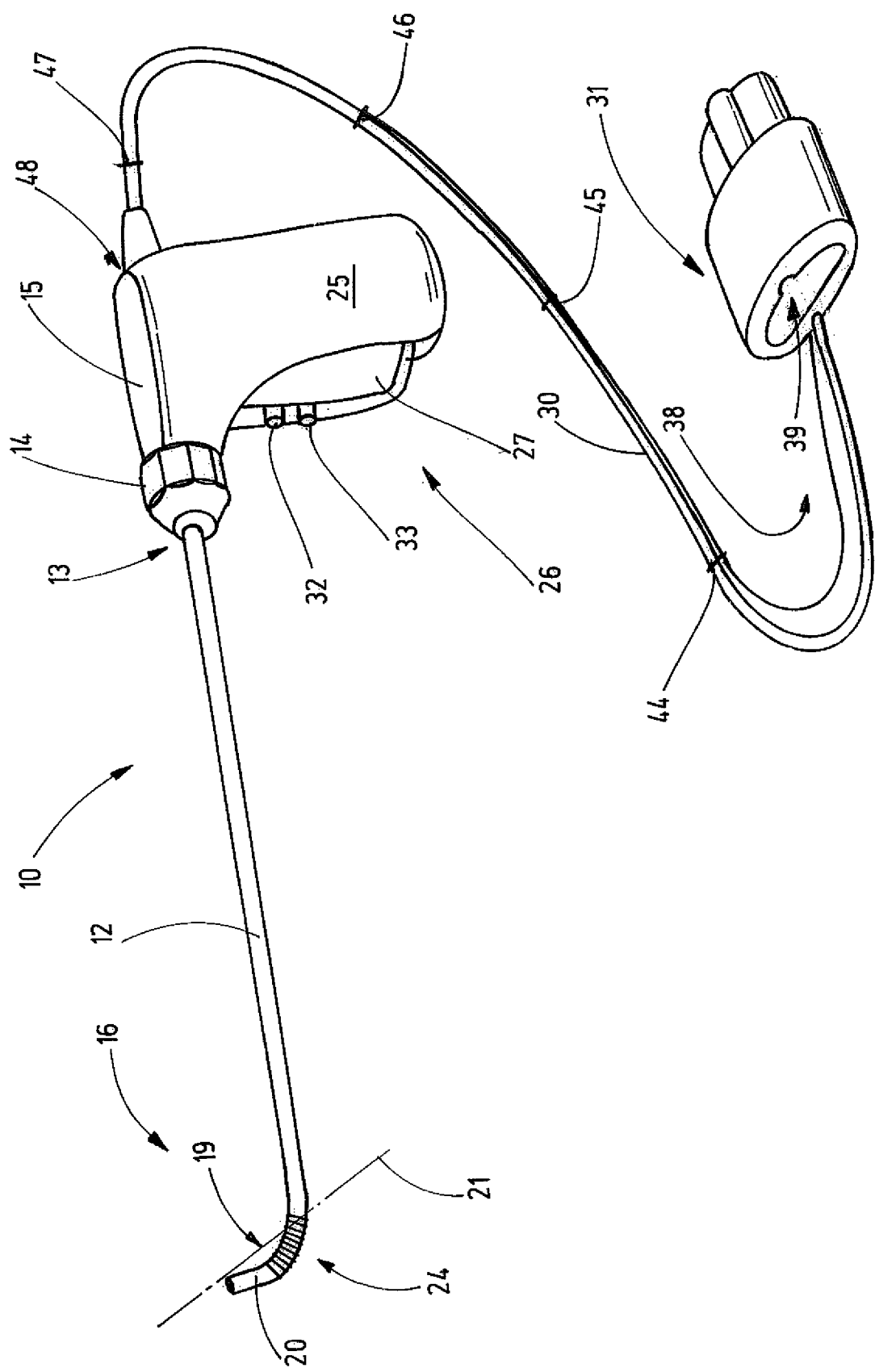

FIG. 2 shows the probe applicator 10 without a probe 11. For better illustration of the basic design of the probe applicator 10, said applicator is again shown with a probe 11 by a schematic basic representation.

The shaft 12 consists of a slim tube having a diameter that preferably does not exceed 5 mm and having a length that is preferably greater than 200 mm. The shaft length may be up to 500 mm and, in special cases, even more. The tube, of which the shaft 11 consists, may be of metal or plastic material and preferably has such a stiffness that said tube, when being inserted through a small opening into the body of the patient, can be positioned and moved by moving its proximal end 13 inside the body, so that the distal end 16 of the shaft 12 takes the desired positions or performs the desired movements. In any event, the shaft 12 is substantially stiffer compared to the flexible probe 11 that, typically, is provided for the endoscopic use and that extends through a longitudinally continuous lumen 14 of the shaft 12, so that one end 18 of said probe may project out of the shaft 12.

The shaft 12 may comprise a flexible section 19 that is shown separately in FIG. 4. It is disposed to angle the end of the shaft 12, said end potentially being a stiff tube section 20. Thus, the distal end of the shaft may be converted from a straight (elongated) form into an arcuate form that curves about an axis of curvature 21 that is oriented transversely with respect to the shaft 2 and extends outside of said shaft.

As is schematically indicated in FIG. 4, the flexible section 19 may display different axial stiffness on diametrically opposite sides. For example, it may comprise a well compressible region 22 on the side facing the axis of curvature 21, while it may feature a less longitudinally compressible region 23 on the opposite side. Considering this configuration, the flexible section 19 forms a bending device 24. However, it may also be configured in a different manner that allows a targeted conversion of the distal end of the shaft from an elongated form into an angled form.

For actuating the bending device 24, there is provided—in or on the housing 15 having the handle 25—an actuating device 26, for example in the form of a lever 27 that is pivotally supported in or on the housing 15. This lever or any other handling means can transmit—via suitable gearing that comprises a force-transmitting means 28, for example in the form of a pulling means 29—an actuating force of the actuating device 26 to the bending device 24. To do so, for example, the pulling means 29 may be connected directly, or via suitable gearing, proximally to the lever 27 and distally to the end section 20, in which case said pulling means extends from the housing 15 through the shaft 12 up to the distal end 16 of the shaft 12. If said pulling means is tensioned, it compresses the region 22 in axial direction, which is why the flexible section 19 bends in lateral direction.

Furthermore, via a cable 30, the housing 15 is connected to a plug 31 that is disposed for connecting the probe applicator 10 to a supply device. The latter is disposed to supply the probe 11 with the necessary operating medium, for example an electrical voltage and/or a liquid or gaseous fluid or also a vacuum. Furthermore, the plug 31 may be disposed to transmit control signals from the probe applicator 10—in particular from the control elements 32, 33 provided on said applicator—to the supply device. For example, the control elements 32, 33 may be electrical switches whose switch status can be output to appropriate pins 36, 37 on the plug 31 via lines 34, 35 (FIG. 5) that extend through the cable 30. For example, the switch 32 can clear the flow of current via a diode in one flow direction between the two lines 34, 35, while the switch 33 will clear the flow of current via another oppositely poled diode in the opposite direction between the two lines 34, 35. In this manner, it is possible to distinguish on the two pins 36, 37 whether no switch, one switch or both switches are actuated. Other switch arrangements are possible, e.g., all the switches may be connected to one common reference potential line and to one individual signal line.

Instead of the electrical lines 34, 35, there may also be provided one or more other signal lines, for example optical waveguides or the like, in which case at least one control element 32 and/or 33 may influence, for example, the reflection properties at the end of one such optical waveguide in order to effect a signal delivery.

The plug 31 comprises a connecting device 38 for the probe 11. The connecting device 38 may be, for example, an opening 39 provided in the plug 31, into which opening a probe plug 40 provided on the proximal end of the probe 11 can be inserted. This probe plug is disposed to supply the probe 11 with its operating medium. For example, the probe plug 40, as illustrated in a first modification in FIG. 5, comprise an electrical contact 41 which is associated with the contact jack 42 provided in the opening 39 or with other contact means. This contact jack 42 is electrically connected to a corresponding pin 43 of the plug 31.

As can be inferred from FIGS. 1 and 2, in particular, the probe 11 may be connected to the cable 30 by suitable clamps 44 to 47 or by other suitable means. Then the probe extends—starting from the connecting device 38—through the housing 15 and the shaft 12 up to the distal end 20 of the shaft 12. As can be inferred from FIG. 3, a locking device 48 may be provided in or on the housing 15, said locking device being manually actuatable in order to selectively clear or block an axial movement of the probe 11. For example, the locking device 48 may be a clamping device, for example in the form of an eccentric clamping lever 49, located opposite a counter-bearing 50. The probe 11 is located between the counter-bearing 50 and the clamping lever 49 and can be appropriately fixed in place by actuating the clamping lever 49.

The probe applicator described so far works as follows:

For its use, a probe 11 is inserted through an appropriate insertion opening 51 (FIG. 3)—located opposite the proximal end 13 of the shaft 12 and in straight extension thereof—into the housing 15 and through said housing into the lumen 17. In doing so, the probe 11 is initially advanced preferably to such an extent that its distal end 18 projects from the end section 20 or stops shortly before its mouth. In this position, the probe 11 may be locked in place with the locking device 48. Before or after this measure, the probe plug 40 is inserted into the connecting device 38, and the plug 31 is connected to the supply device. Optionally, the desired operating mode is selected on the device. Thus, the probe applicator 10, with the probe 11 inserted, is ready for operation.

The distal end 16 of the shaft 12 can be inserted through an opening, for example a cut, into a patient, in which case the probe applicator 10 is held by the user by the handle 25 and positioned by means of said handle. If desired, the user can bend the distal end 16 of the shaft 12 by means of the actuating device 26 in order to bring the distal end 18 of the probe 11 into a desired angular position. Furthermore, the user can rotate the shaft 12 about its longitudinal end when the end is bent. Furthermore, if desired, the user can release the clamping device 48 and advance the or retract the probe 11 further. By means of the control elements 32, 33, the user can cause the supply device to activate or deactivate the probe 11. For example, by means of the control elements 32, 33, the user can switch the power on or off, or select and activate, as well as deactivate various modes, for example, levels of voltage, forms of voltage (curve forms, crest factors).

The connecting device 38 is not restricted to the supply of electrical probes. For example, said device may comprise, additionally or alternatively to the contact means 32, a fluid connection 52, for example in the form of a fluid connector. The latter can be connected—via a suitable channel—to a fluid plug pin 53 that, preferably, extends parallel to the contact pins 36, 37, 43 away from the plug 31. Accordingly, a probe 11a may be provided with a fluid plug pin 54 that is associated with the fluid connection 52. Again, in addition, it is possible to provide an electrical contact 41. In this case, the control elements 32, 33 may be disposed to activate or deactivate the fluid supply and the power supply of the probe 11a, independently of each other.

As is obvious from FIG. 6, the connecting device 38 need not necessarily be provided directly on the plug 31. It is also possible to provide a separate connector arrangement that is connected to the plug 31 via a line 55. Another alternative is to provide the connecting device 38 on the supply device itself. Other than that, the description hereinabove applies analogously.

According to the invention, there is provided a probe applicator 10 disposed for receiving flexible probes 11, 11a that are intended for endoscopic use and can be made accessible with the probe applicator for laparoscopic use. The control of the device supplying the probes 11, 11a occurs via control elements 32, 33 of the probe applicator 10. Preferably, the probe 11, 11a is supplied via a connecting device 38 provided on the probe applicator 10.

LIST OF REFERENCE SIGNS

| | |
|---|---|
| 10 | Probe applicator |
| 11 | Probe |
| 12 | Shaft |
| 13 | Proximal end of the shaft 12 |
| 14 | Shaft receptacle |
| 15 | Housing |
| 16 | Distal end of the shaft 12 |
| 17 | Lumen |
| 18 | Distal end of the probe 11 |
| 19 | Flexible section of the shaft 12 |
| 20 | End section of the shaft 12 |
| 21 | Axis of curvature |
| 22 | Axially yielding region |
| 23 | Axially stiff region |
| 24 | Bending device |
| 25 | Handle |
| 26 | Actuating device |
| 27 | Lever |
| 28 | Force-transmitting means |
| 29 | Pulling means |
| 30 | Cable |
| 31 | Plug |
| 32, 33 | Control elements |
| 34, 35 | Lines |
| 36, 37 | Pins |
| 38 | Connecting device |
| 39 | Opening |
| 40 | Probe plug |
| 41 | Electrical contact |
| 42 | Contact means |
| 43 | Pin of the plug 31 |
| 44-47 | Clamps |
| 48 | Locking device |
| 49 | Eccentric clamping lever |
| 50 | Counter-bearing |
| 51 | Insertion opening |
| 52 | Fluid connection |
| 53 | Fluid plug pin |
| 54 | Fluid plug pin |
| 55 | Line |

The invention claimed is:

1. A probe applicator (10) for the laparoscopic use of flexible probes (11, 11a), comprising:
 a housing (15) having a handle (25) for manually positioning and moving the probe applicator (10) relative to a patient,
 a shaft (12) in the form of an elongated, stiff tube which is connected on a proximal end (13) thereof to a shaft receptacle (14) provided on the housing and which is open on a distal end (16) thereof,
 at least one control element (32, 33) arranged on the housing (15) so as to be manually accessible,
 a cable (30) that extends from the housing (15) to a plug (31) having at least one plug connector (36) and contains at least one signal line (34) that connects the at least one control element (32) to a plug contact (36),
 a probe insertion opening (51) provided on the housing (15), said opening being located opposite the shaft receptacle (14), and
 a connecting device (38) that is configured for the connection of a probe (11, 11a) to supply said probe with an operating medium, wherein the connecting device (38) is arranged on the plug (31).

2. A probe applicator according to claim 1, wherein the shaft (12) has a diameter and has a length between twenty and 300 times the diameter of the shaft (12).

3. A probe applicator according to claim 1, wherein a bending device (24) is arranged on the distal end (16) of the shaft (12) which is connected to an actuating device (26) arranged on the housing (15).

4. A probe applicator according to claim 3, wherein the actuating device (26) is a pivoting lever (27) arranged on the handle (25), said lever being connected to the bending device (24) via a force-transmitting means (28).

5. A probe applicator according to claim 3, wherein the bending device (24) has a flexible section (19) configured to be shifted from an elongated form to an arcuate form.

6. A probe applicator according to claim 3, wherein the bending device (24) has a stiff straight tube section (20) on a distal end of the bending device.

7. A probe applicator according to claim 1, wherein the shaft (12) is connected to the housing (15) so as to be rotatable about a longitudinal axis of the shaft.

8. A probe applicator according to claim 1, wherein a locking device (48) is arranged on the probe insertion opening (51) for axially fixing in place the probe (11, 11a) extending through the probe insertion opening (51).

9. A probe applicator according to claim 8, wherein the locking device (48) is a clamping device (49) that is configured to be manually actuated.

10. A probe applicator according to claim 1, wherein the at least one signal line (34) is an electrical line, and the at least one plug connector is an electrical plug contact (36).

11. A probe applicator according to claim 1, wherein the cable (30) includes connecting means (44-47) for receiving the probe (11, 11a).

12. A probe applicator according to claim 1, wherein the connecting device (38) includes at least one fluid connection (52).

13. A probe applicator according to claim 1, wherein the connecting device (38) comprises at least one electrical connection (42).

14. The probe applicator according to claim 1, where the connecting device (38) comprises an opening (39) disposed on the plug (31) that is sized and configured to receive a probe plug (40) of the probe (11, 11a).

* * * * *